United States Patent [19]

Nakamoto et al.

[11] 4,060,527
[45] Nov. 29, 1977

[54] PYRIDO[2,3-C]-ACRIDINE-1-HYDROXY-2-CARBOXYLIC ACID DERIVATIVES

[75] Inventors: Hiromasa Nakamoto, Takaoka; Shin-Ichi Nakamoto, Oyabe; Hidemitu Amemiya, Takaoka; Souji Miyamura, Takaoka; Motoo Shiba, Takaoka; Nobuko Nakamura, Takaoka, all of Japan

[73] Assignee: Fuji Chemical Industries, Ltd., Japan

[21] Appl. No.: 589,772

[22] Filed: June 23, 1975

[51] Int. Cl.² .................. C07D 471/04; A61K 31/47
[52] U.S. Cl. ............................ 260/279 R; 424/257
[58] Field of Search .................................. 260/279 R

[56] References Cited

U.S. PATENT DOCUMENTS

| 2,477,048 | 6/1949 | Dobson et al. | 260/279 R |
| 3,300,499 | 1/1967 | Lesher | 260/287 |
| 3,313,817 | 4/1967 | Lesher | 260/287 |
| 3,907,798 | 9/1975 | Lesher | 260/251 A |

OTHER PUBLICATIONS

Dobson et al, Chemical Abstracts, 40 4377⁸ (1946).
Kermack et al, Chemical Abstracts, 36 3803⁸ (1942).
Dobson et al., Chemical Abstracts 42 4590 (1948).

*Primary Examiner*—Donald G. Daus
*Assistant Examiner*—Diana G. Rivers
*Attorney, Agent, or Firm*—Wenderoth, Lind & Ponack

[57] ABSTRACT

Novel compound of the following formula

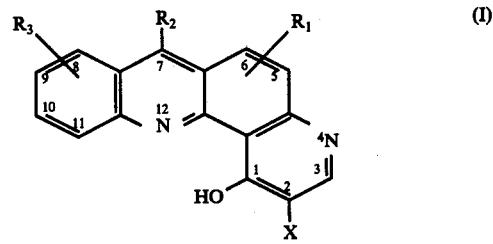

wherein X is a member selected from the group consisting of carboxy and carbalkoxy and each or $R_1$, $R_2$ and $R_3$ is a member selected from the group consisting of hydrogen, alkyl, alkenyl, aryl, alkoxy, hydroxy, halo, amino, alkylamino, alkylmercapto, nitro, cyano, alkylsulfonyl, carboxy, carbalkoxy, hydroxyalkyl, aminoalkyl, hydroxyalkylamino, and acetoxyalkylamino, and pharmaceutically acceptable acid addition salts thereof. The above compound can be prepared by heating a 3-(substituted amino)-acridine to cyclize said compound, and if desired, hydrolyzing the resulting product and/or it with an acid.

3 Claims, No Drawings

PYRIDO[2,3-C]-ACRIDINE-1-HYDROXY-2-CARBOXYLIC ACID DERIVATIVES

This invention relates to novel acridine derivatives having a wide antimicrobial spectrum against Gram-positive and Gram-negative microorganisms, superior antimicrobial activity and extremely low toxicity. These novel compounds are useful in medical and other fields as antimicrobial substances, and also find utility as intermediates for syntheses.

More specifically, this invention relates to compounds of the following formula

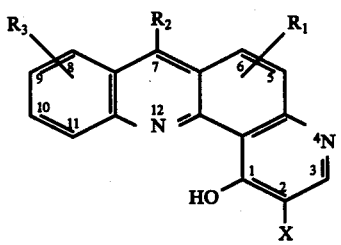

wherein X is a member selected from the group consisting of carboxy and carbalkoxy, and each of $R_1$, $R_2$ and $R_3$ is a member selected from the group consisting of hydrogen, alkyl, alkenyl, aryl, alkoxy, hydroxy, halo, amino, alkylamino, alkylmercapto, nitro, cyano, alkylsulfonyl, carboxy, carbalkoxy, hydroxyalkyl, aminoalkyl, hydroxyalkylamino and acetoxyalkylamino, and their pharmaceutically acceptable acid addition salts.

Previously, acriflavin which is a mixture of 2,8-diamino-10-methylacridinium chloride and 2,8-diaminoacridine and its hydrochloride have been known as antimicrobial agents. These compounds exhibit antibacterial properties against Gram-positive bacteria, but the activity is not so high as to be entirely satisfactory. On the other hand, these compounds show only low antibacterial properties against Gram-negative bacteria. Thus, these compounds are defective both in antibacterial spectrum and antibacterial activity. In addition, they have fairly high toxicity, and exhibit high toxicity in internal administration. This has limited their application only to externally administrable pharmaceuticals.

We have made extensive work in order to develop acridine derivatives free from the above defects and disadvantages, and found that the acridine derivatives of formula (I) above can be prepared in high yields and purities by a simple procedure of heat-cyclizing 3-substituted amino-acridine or derivatives thereof derived from 3-amino-acridine or derivatives thereof and malonic acid diesters. It has also been found that the resulting compounds of formula (I) have a wide antimicrobial spectrum against Gram-positive and Gram-negative microorganisms and superior antimicrobial activity. We have ascertained furthermore that the compounds of formula (I) have very low toxicity, ensure safety, and because of the superior spectrum and activity, are very useful as pharmaceuticals for animals such as humans, domestic animals, and poultry.

Heretofore, 1-N-substituted naphthylidin derivatives have been known as widely used antibacterial agents, a typical example of which is Nalidixic acid of the following formula

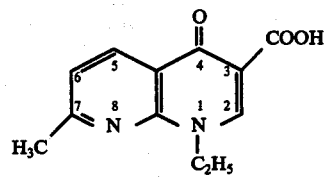

(see, for example, G. Y. Lesher et al., J. Medicinal and Pharmaceutical Chemistry, Vol. 5, 1962, pages 1063 to 1065). It is known that these conventional antibacterial agents represented by the commercially available compound of the above formula show a fairly good activity in vitro (MIC) of 5.0 to 12.5 mcg./ml. against Gram-negative bacteria such as *Escherichia coli*, but their activity in vitro against Gram-positive bacteria such as *Staphylococcus aureus* is as poor as 50.0 to 100.0 mcg./ml. In contrast, the compounds of formula (1) of this invention are unique in that they exhibit superior antimicrobial activities both against Gram-negative bacteria and against Gram-positive bacteria. It is further noteworthy that the compounds of formula (1) have far lower toxicity in terms of acute toxicity ($LD_{50}$) than the above known antibacterial agents.

U.S. Pat. No. 3,313,817 to G. Y. Lesher et al, the authors of the above-cited article, disclose that 1-N-alkyl or alkenyl substituted phenanthroline derivatives of the following formula

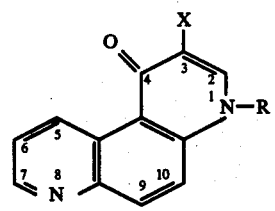

wherein X is carboxy or lower carbalkoxy, and R is lower alkyl or lower alkenyl, have antibacterial properties. The Patent discloses the following 1-N-unsubstituted phenanthrolline derivatives

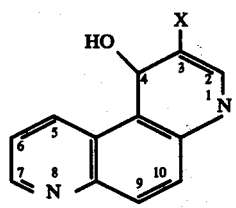

wherein X is carboxy or lower carbalkoxy, as a starting material for the above compound, and the following 1-N-unsubstituted phenanthroline derivatives

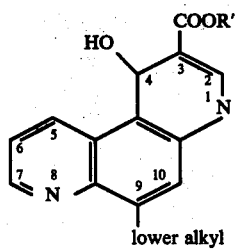

lower alkyl wherein R' is hydrogen or lower alkyl, as an intermediate. It however fails to give any description as to whether the above starting material and the intermediate are pharmaceutically effective substances. The compounds which the Patent discloses have antibacterial properties are all 1-N-substituted derivatives. According to our experimentation, these starting material and intermediate do not show any antibacterial activity against both Gram-positive and Gram-negative microorganisms.

The article of G. Y. Lesher et al. cited above states that the 1-N-substituted derivatives have antibacterial properties. Thus, the above two references commonly disclose that only the 1-N-substituted derivatives have antibacterial properties.

Our works have shown that as regards the acrididine derivatives of formula (I) of this invention which have a different skeletal structure from the naphthylidin derivatives or phenanthroline derivatives described in the above-cited references, 4-N-unsubstituted compounds show superior antimicrobial properties and for example, 4-N-ethyl substituted compounds do not substantially exhibit antimicrobial properties.

Accordingly, it is an object of this invention to provide novel compounds of formula (I) and a process for their preparation.

Another object of this invention is to provide an antimicrobial composition for animals (e.g., humans, domestic animals, or poultry) comprising the novel compound of formula (I) as an active ingredient.

Still another object of this invention is to provide a method for treating diseases of animals induced by pathogenic bacteria using the novel compound of formula (I).

The above and other objects of this invention along with its advantages will become more apparent from the following description.

In the compounds of formula (I) of this invention, X is selected from the group consisting of carboxy and carbalkoxy. Preferably, the alkoxy moiety of the carbalkoxy has 1 to 6 carbon atoms. Examples of the alkoxy are methoxy, ethoxy, n-propoxy, iso-propoxy, n-butoxy, iso-butoxy, tert-butoxy, n-pentoxy, iso-pentoxy, neo-pentoxy, tert-pentoxy, n-hexoxy, iso-hexoxy, and other isomers of these alkoxy groups. Alkoxy with 1 to 3 carbon atoms is more preferred. Carboxy is most preferred as X.

$R_1$, $R_2$ and $R_3$ in the formula (I) are identical or different, and represent a member selected from the group consisting of hydrogen, alkyl, alkenyl, aryl, alkoxy, hydroxy, halo, amino, alkylamino, alkylmercapto, nitro, nitrilo, alkylsulfonyl, carboxy, carbalkoxy, hydroxyalkyl, aminoalkyl, hydroxyalkylamino and acetoxyalkylamino. The alkyl preferably contains 1 to 10 carbon atoms, and more preferably, 1 to 6 carbon atoms. Specific examples of the alkyl groups are those corresponding to the $C_1$ to $C_6$ alkoxy groups exemplified above, heptyl, octyl, nonyl, decyl, and isomers of these groups.

Preferably, the alkenyl has 2 to 6 carbon atoms, such as vinyl, allyl, propenyl, butenyl, pentenyl, hexenyl, and isomers of these. Alkenyl groups with 2 or 3 carbon atoms are more preferred.

Preferred aryl groups are those containing 6 to 10 carbon atoms which may contain a substituent selected from the group consisting of $C_1 - C_5$ lower alkyl, halo, nitro, alkylamino with the alkyl moiety containing 1 to 5 carbon atoms, hydroxy, and $C_1 - C_5$ lower alkoxy. Specific examples of the aryl are phenyl and naphthyl which may contain the above substituent.

Preferably, the alkoxy contains 1 to 6 carbon atoms, and more preferably 1 to 3 carbon atoms. Specific examples of the alkoxy are the same as those exemplified with regard to the alkoxy of the carbalkoxy X.

Examples of the halo are Cl, Br, I and F.

Preferred alkylamino groups are those containing 1 to 4 carbon atoms. Specific examples of the alkylamino are those containing alkyl groups corresponding to the alkoxy groups exemplified above with regard to the alkoxy of the carbalkoxy X. These alkylamino groups include mono- and dialkylamino groups.

Preferred alkylmercapto groups are those in which the alkyl moiety contains 1 to 6 carbon atoms, especially 1 to 3 carbon atoms. Specific examples of the alkylmercapto are those in which the alkyl moiety corresponds to the alkoxy of the carbalkoxy X exemplified above.

Preferred alkylsulfonyl groups are those in which the alkyl moiety contains 1 to 2 carbon atoms.

Preferred carbalkoxy groups are the same as those described above with regard to group X.

Preferred hydroxyalkyl groups are those in which the alkyl moiety contains 1 to 6 carbon atoms, especially 1 to 3 carbon atoms. Specific examples of the hydroxyalkyl are those in which the alkyl moiety is the same preferred species as mentioned above with regard to the alkyl in the alkylmercapto.

Preferred aminoalkyl groups are those which contain 1 to 3 carbon atoms, such as methyl, ethyl, or n- or iso-propyl.

Preferred (hydroxyalkyl)amino groups are mono- or di-(hydroxyalkyl)amino groups with 1 to 2 carbon atoms.

Preferred acetoxyalkylamino groups are mono- or di-(acetoxyalkyl)amino groups in which the alkyl moiety contains 1 to 2 carbon atoms.

The compounds of formula (I) can easily form addition salts with organic or inorganic acids. The compounds of formula (I) include these addition salts, preferably those which are pharmaceutically acceptable. Examples of these acids are inorganic acids such as hydrochloric acid, sulfuric acid, phosphoric acid, hydrobromic acid, or nitric acid, and organic acids such as acetic acid, propionic acid, lactic acid, butyric acid, malonic acid, tartaric acid, succinic acid or phthalic acid.

The compounds of formula (I) of this invention can be easily obtained in high yields and high purities by heating 3-(substituted amino)-acridines of the following formula

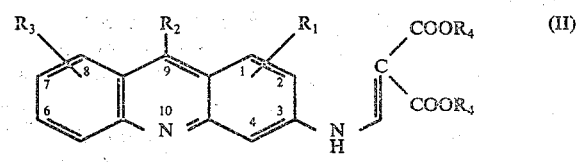

wherein $R_1$, $R_2$ and $R_3$ are the same as defined in formula (I), and $R_4$ is an alkyl group, preferably containing 1 to 6 carbon atoms, more preferably containing 1 to 3 carbon atoms, to cyclize them.

The compounds of formula (II) can be easily prepared, for example, by reacting 3-amino-acridines of the following formula

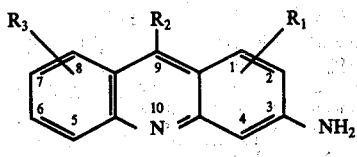

wherein $R_1$, $R_2$ and $R_3$ are the same as defined with regard to formula (I), with derivatives of malonic acid diesters of the following formula

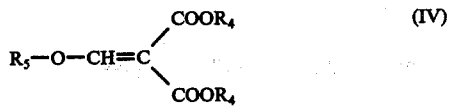

wherein $R_4$ is the same as defined in formula (II), and $R_5$ is the same as $R_4$.

In the present invention, the compound of formula (II) may be isolated from the reaction product between the compounds of formulae (III) and (IV), and used for preparing the compound of formula (I). Or it may be used as a material for the compound of formula (I) without isolating it from the reaction product. Compounds of formula (I) in which group X is carboxy can be prepared by hydrolyzing pyrido[2,3-c]-acridine-1-hydroxy-2-carbalkoxy compound or its derivative of the following formula

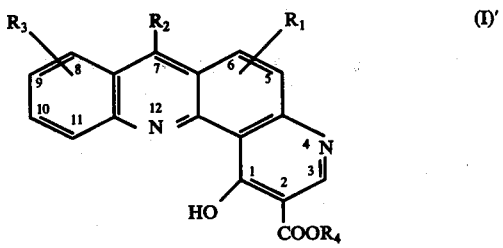

wherein $R_4$ is the same as defined in formula (II), with acids or alkalies in a customary manner. Examples of the acids are mineral acids such as hydrochloric acid, or sulfuric acid, and examples of the alkalies are sodium hydroxide, potassium hydroxide and calcium carbonate. The hydrolyzing temperature is not critical, but the hydrolysis can be promoted by heating.

Acid addition salts of the compounds of formula (I) can be prepared easily by contacting the compounds of formula (I) with acids of the type exemplified above.

The reaction of the 3-amino-acridines of formula (III) with the derivative of malonic acid diesters of formula (IV) can be carried out in the presence or absence of a solvent. Usually, however, it is carried out in a solvent. A wide variety of organic solvents, such as benzene, toluene, xylene, chloroform, carbon tetrachloride, methylene chloride, tetrachloroethane, trichloroethylene, diethyl ether, dioxane, tetrahydrofuran, methanol, iso-propanol, ethylene glycol, and diethylene glycol can be used for this purpose.

When the derivative of malonic acid diester of formula (IV) is liquid under the reaction conditions, it can concurrently serve as a solvent.

There is no particular limitation on the reaction temperature, and the reaction can be performed at room temperature. Preferably, however, the reaction is carried out at an elevated temperature. Thus, the reaction temperature is usually room temperature to about 250° C., preferably about 50° C. to about 150° C., and most preferably at the boiling point of the solvent or under reflux. Preferably, the reaction time is about 5 to about 150 minutes.

The molar ratio between the compound of formula (III) and the compound of formula (IV) to be reacted can be suitably selected, and for example, about 1 to about 10 mols of the compound of formula (IV) is used per mol of the compound of formula (III).

The reaction product can be directly subjected to the cyclization reaction, but if desired, isolated by cooling prior to the cyclization reaction. The compound of formula (II) isolated can be purified by a recrystallizing procedure using an organic solvent.

Preferably, the cyclization of the compound of formula (II) is performed in an organic solvent having the highest possible boiling point. The reaction proceed merely by heating, and preferably at a temperature of about 100° to about 500° C., more preferably about 150° to about 500° C., and most preferably at the boiling point of the solvent or under reflux. The preferred reaction time is about 10 to about 180 minutes. The reaction pressure is atmospheric pressure or the reaction can be performed under a high pressure. Examples of the organic solvent are o-dichlorobenzene, diphenyl, diphenyl ether, and Dowtherm A (a trademark for a eutectic mixture consisting of 1 part of diphenyl and 3 parts of diphenyl ether).

The reaction mixture resulting from the reaction may, if desired, be cooled after addition of a non-aqueous solvent such as n-hexane or n-pentan, and the precipitate formed may be separated and collected.

As stated hereinabove, the reaction mixture containing the resulting compound of formula (I') can be converted to a compound of formula (I) in which X is carboxy by hydrolysis without particularly purifying it.

The antibacterial activities (MIC, mcg/ml) and acute toxicities $LD_{50}$ (mg/Kg) on mouse of some examples of the compounds of formula (I) and the conventional antibacterial agent, Nalidixic acid, were determined, and the results are shown in Table 1 below. In the determination, Staphylococcus aureus was used as a Gram-positive bacterium, and Escherichia coli as a Gram-negative bacterium.

Table 1

| Compound | Staphylococcus aureus | | Escherichia coli | | Acute toxicity on mice (LD$_{50}$:mg/Kg) | | |
|---|---|---|---|---|---|---|---|
| | bacterio-static action (mcg/ml) | bacteri-cidal action (mcg/ml) | bacterio-static action (mcg/ml) | bacteri-cidal action (mcg/ml) | peroral (P.O.) | sub-cutaneous (s.c.) | intra-vaneous (i.v.) |
| (No. F-631) | 1.25 | 1.25 | 1.25 | 1.25 | >5,000 | >3,000 | 230 |
| (No. F-632) | 1.25 | 2.50 | 0.62 | 1.25 | >5,000 | >3,000 | 253 |
| (No. F-633) | 1.25 | 1.25 | 1.25 | 1.25 | >5,000 | >3,000 | 245 |
| (No. F-634) | 0.25 | 0.25 | 0.62 | 0.62 | >5,000 | >3,000 | 215 |
| (No. F-635) | 0.62 | 0.62 | 1.25 | 1.25 | >5,000 | >3,000 | 186 |
| (No. F-636) | 1.25 | 1.25 | 1.25 | 2.50 | >5,000 | >3,000 | 235 |

Table 1-continued

| Compound | *Staphylococcus aureus* bacteriostatic action (mcg/ml) | *Staphylococcus aureus* bactericidal action (mcg/ml) | *Escherichia coli* bacteriostatic action (mcg/ml) | *Escherichia coli* bactericidal action (mcg/ml) | Acute toxicity on mice (LD₅₀:mg/Kg) peroral (P.O.) | Acute toxicity on mice (LD₅₀:mg/Kg) subcutaneous (s.c.) | Acute toxicity on mice (LD₅₀:mg/Kg) intravaneous (i.v.) |
|---|---|---|---|---|---|---|---|
| 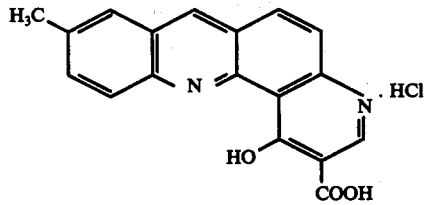 (No. F-637) | 1.25 | 2.50 | 0.62 | 1.25 | >5,000 | >3,000 | 256 |
| 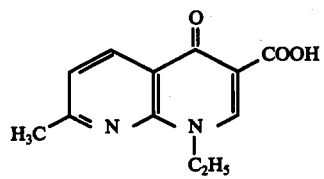 (Comparison: Nalixidic acid) | 125.0 | — | 6.25 | 6.25 | 3,300 | 500 | 176 |

It can be seen from Table 1 that the compounds of formula (I) have superior activities against Gram-positive and Gram-negative bacteria, and a broad antibacterial spectrum against both types of pathogenic bacteria, and exhibit low toxicity to warm-blooded animals. For example, the compounds of formula (I) of this invention exhibit superior antibacterial activities against Gram-positive bacteria such as *Streptococcus hemolyticus, Diplococcus pneumoniae, Corynebacterium diphtheriae, Bacillus anthracis, Clostridium tetani,* or *Clostridium welchii* and Gram-negative pathogenic bacteria such as *Neisseria gornorrhoeae, Neisseria meningitidis, Salmonella typhosa, Shigella flexneri, Shigella sonnei, Vibrio comma, Klebsiella pneumoniae, Proteus vulgaris, Pseudomonas aeruginosa* or *Haemophilus influenzae.*

The compounds of formula (I) of this invention can be utilized as pharmaceuticals in various formulations using a pharmaceutically acceptable carriers or diluents. These formulations include orally administrable forms such as powders, granules, tablets, emulsions or suspensions, forms usable in the oral cavity as troche, preparations for intramuscular or hypodermic injections, forms suitable for application through mucous membranes such as bucchal tablets and suppositories; and externally applicable forms such as ointments, pastes or liquids.

Examples of the liquid or solid carriers or diluents used for formulation are lactose, glucose, sucrose, dextrin, starch, calcium carbonate, magnesium oxide, sodium bicarbonate, kaolin, bentonite, talc, gelatin, tragacanth rubber, gum arabic, carboxylmethyl cellulose, alkali metal salts of carboxymethyl cellulose, agar, sodium alginate, stearic acid, magnesium or calcium stearate, aluminum silicate, alumina gel, water, ethanol, benzyl alcohol, stearyl alcohol, polyethylene glycol, propylene glycol, polyvinyl pyrrolidone, glycerol, animal oils and fats such as lard, Vaseline, vegetable oils such as castor oil or coconut oil, isotonic sodium chloride solution, phosphate buffers, emulsifiers, bees wax, liquid paraffins, and lanolin.

The concentration of the compound of formula (I) of this invention in these formulations can be varied optionally, and for example, it can be used in a concentration of 0.01 to 99% by weight, preferably about 0.1 to about 90% by weight, based on the total weight of the ingredients. Usually, the concentration is about 0.1 to about 50% by weight.

The dose of the compound of formula (I) can be varied over a wide range, for example, about 5 to about 100 mg/Kg body/day, preferably about 10 to about 60 mg/Kg body/day.

Since the compound of formula (I) is of low toxicity, it can be applied in larger doses.

The compounds of this invention are useful not only as antimicrobial substances against pathogenic bacteria on man and other animals, but also as antimicrobial substances against noxious bacteria, viruses and fungi in other fields such as foodstuffs, agriculture and horticulture, textiles, leathers, oils and fats, paints, or varnishes.

Compounds of formula (I) containing the following basic structure

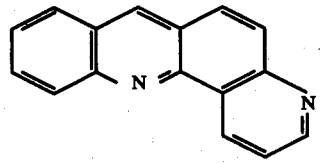

have not been known heretofore, and their antimicrobial activities have neither been known.

The following Examples further illustrate the embodiments of this invention.

EXAMPLES OF SYNTHESIS

Example 1

1. 3.9 g of 3-aminoacridine [III] was mixed with 4.3 g of diethyl ethoxymethylenemalonate [IV], and the mixture was heated on an oil bath at 110° to 115° C. for 1 hour. The resulting viscous light brown reaction mixture was solidified by allowing it to cool. The solidified mixture was recrystallized from a mixture consisting of 20 ml. of benzene and 80 ml. of n-hexane to afford 6.2 g of 3-(β-diethoxycarbonylvinylamino)-acridine [II] as yellow crystals. The melting point of the product was 130° to 132° C. The elemental analysis values for $C_{21}H_{20}N_2O_4$ were as follows:

|  | C(%) | H(%) | N(%) |
|---|---|---|---|
| Calculated: | 69.23 | 5.49 | 7.67 |
| Found: | 69.31 | 5.54 | 7.73 |

2. 3.6 g of the 3-(β-diethoxycarbonylvinylamino)-acridine obtained in (1) above was mixed with 36 ml. of diphenyl ether, and the mixture was heated under reflux at 260° to 270° C. for 20 minutes. After cooling, 145 ml. of n-hexane was added, and the precipitated crystals were collected by filtration. The crystals were recrystallized from ethanol to afford 3.9 g of ethyl pyrido[2,3-c]-acridine-1-hydroxy-2-carboxylate as orange yellow needlelike crystals having a melting point of 194° to 196° C.

The elemental analysis values for $C_{19}H_{24}N_2O_3$ were as follows.

|  | C(%) | H(%) | N(%) |
|---|---|---|---|
| Calculated: | 71.70 | 4.40 | 8.80 |
| Found: | 71.84 | 4.52 | 8.75 |

The NMR spectrum of the product in dimethyl sulfoxide was as follows:

δ = 1.42 (triplet, 3H, C$\underline{H}_3$), 4.35 (quartet, 2H, C$\underline{H}_2$), 17.55 (singlet, 1H, O$\underline{H}$).

3. 3.2 g of the ethyl pyrido[2,3-c]-acridine-1-hydroxy-2-carboxylate [I] obtained in (2) above was added to a mixture of 30 ml. of 6N-hydrochloric acid and 30 ml. of acetic acid, and the mixture was heated at 95° to 100° C. for 1 hour. After cooling, the precipitated crystals were collected by filtration. The crystals were washed with ethanol, and then recrystallized from a mixture of 150 ml. of 6N-hydrochloric acid and 150 ml. of acetic acid to afford 2.4 g of pyrido[2,3-c]-acridine-1-hydroxy-2-carboxylic acid.hydrochloride as light brown needle-like crystals having a melting point of 322° to 325° C. The elemental analysis values for $C_{17}H_{11}N_2O_3Cl$ were as follows:

|  | C(%) | H(%) | N(%) | Cl(%) |
|---|---|---|---|---|
| Calculated: | 62.48 | 3.37 | 8.58 | 10.87 |
| Found: | 61.20 | 3.23 | 8.68 | 10.81 |

Example 2

1. 2.1 g of 3-amino-2-methyl-acridine [III] was mixed with 2.2 g of diethyl ethoxymethylenemalonate, and the mixture was heated on a water bath at 95° to 100° C. for 1.5 hours. The reaction mixture was cooled and solidified, and recrystallized from a mixture of 17 ml. of ethanol and 50 ml. of n-hexane to afford 2.5 g of 3-(β-diethoxycarbonylvinylamino)-2-methylacridine [II] as yellow needle-like crystals having a melting point of 160° to 162° C. The elemental analysis values for $C_{22}H_{22}N_2O_4$ were as follows:

|  | C(%) | H(%) | N(%) |
|---|---|---|---|
| Calculated: | 69.84 | 5.82 | 7.41 |
| Found: | 69.77 | 5.96 | 7.35 |

2. 2.0 g of the 3-(β-diethoxycarbonylvinylamino)-2-methyl-acridine obtained in (1) above was mixed with 20 ml. of diphenyl ether, and the mixture was heated under reflux at 260° to 270° C. for 20 minutes. The reaction mixture was cooled, and then 80 ml. of n-hexane was added. The resulting crystals were collected by filtration, and recrystallized from 120 ml. of ethanol to afford 1.2 g of ethyl pyrido[2,3-c]-acridine-1-hydroxy-5-methyl-2-carboxylate [I] as orange yellow needle-like crystals having a melting point of 198° to 200° C.

The elemental analysis values for $C_{20}H_{16}N_2O_3$ were as follows:

|  | C(%) | H(%) | N(%) |
|---|---|---|---|
| Calculated: | 72.29 | 4.82 | 8.43 |
| Found: | 72.35 | 4.76 | 8.29 |

The NMR spectrum (CDCl$_3$) of the product was as follows:

δ = 1.50 (triplet, 3H, C$\underline{H}_3$), 4.50 (quartet, 2H, C$\underline{H}_2$), 17.94 (singlet, 1H, -O$\underline{H}$).

3. 1.0 g of the ethyl pyrido[2,3-c]-acridine-1-hydroxy-5-methyl-2-carboxylate obtained in (2) above was added to a mixture consisting of 10 ml. of 6N-hydrochloric acid and 8 ml. of acetic acid, and the mixture was heated at 95° to 100° C. for 2 hours. The reaction mixture was cooled, and then the precipitated crystals were collected by filtration, washed with ethanol, and recrystallized from a mixture of dilute hydrochloric acid and acetic acid to afford 0.7 g of pyrido[2,3-c]-acridine-1-hydroxy-5-methyl-2-carboxylic acid.hydrochloride as light yellow needle-like crystals having a melting point of more than 330° C. The elemental analysis values for $C_{18}H_{13}N_2O_3Cl$ were as follows:

|  | C(%) | H(%) | N(%) | Cl(%) |
|---|---|---|---|---|
| Calculated: | 63.44 | 3,82 | 8.22 | 10.43 |
| Found: | 63.57 | 3.76 | 8.31 | 10.80 |

EXAMPLE 3

1. 1.0 g of 3-amino-9-phenyl-acridine [III] and 0.8 g of diethyl ethoxymethylenemalonate [IV] were melted on an oil bath, and heated at 120° to 125° C. for 30 minutes. When there was no distillation of ethanol, the reaction mixture was allowed to cool. The resulting solidified product was recrystallized from 6.0 ml. of ethanol to afford 1.32 g of 3-(β-diethoxycarbonylvinylamino)-9-phenylacridine [II] as yellow needle-like crystals having a melting point of 150 to 152° C. in a yield of 81.9%.

In the NMR spectrum (CDCl$_3$) of the product two signals were confirmed at δ = 8.72 (duplet, 1H, J=13 cps,

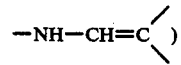

and δ = 11.13 (duplet, 1H, J=13 cps,

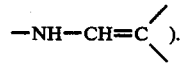

The elemental analysis values for $C_{27}H_{24}N_2O_4$ were as follows:

|  | C(%) | H(%) | N(%) |
|---|---|---|---|
| Calculated: | 73.62 | 5.49 | 6.36 |
| Found: | 73.49 | 5.55 | 6.33 |

2. 7.0 g of the 3-(β-diethoxycarbonylvinylamino)-9-phenylacridine obtained in (1) above was taken into 70 ml. of diphenyl ether, and heated by direct heat under reflux at 255° to 256° C. for 15 minutes, and allowed to cool. The reaction mixture was poured into 50 ml. of m-hexane, when brown cottonlike crystals precipitated. The crystals were collected by suction filtration, and recrystallized from 500 ml. of ethanol to afford 6 g of ethyl pyrido[2,3c]-acridine-1-hydroxy-7-phenyl-2-carboxylate as yellow powdery crystals having a melting point of 164° to 168° C. in a yield of 95.2%.

The NMR spectrum CDCl$_3$ of the product contained four signals at $\delta$ = 1.47 (triplet, 3H, J=7.0 cps, —COOCH$_2$CH$_3$), 4.47 (quartet, 2H, J=7.0 cps, — COOCH$_2$CH$_3$), 9.26 (singlet, 1H, C$_3$—H), and 18.42 (singlet, 1H, C$_1$—OH).

The elemental analysis values for $C_{25}H_{18}N_2O_3$ were as follows:

|  | C(%) | H(%) | N(%) |
|---|---|---|---|
| Calculated: | 76.13 | 4.60 | 7.10 |
| Found: | 76.40 | 4.51 | 7.15 |

3. 1.0 g of the ethyl pyrido[2,3c]-acridine-1-hydroxy-7-phenyl-2-carboxylate obtained in (2) above was taken into a 1:1:1 mixture of water, acetic acid and conc. hydrochloric acid, and heated at 80° C. for 30 minutes. The reaction mixture was cooled, and then treated with 10% aqueous solution of sodium hydroxide to adjust its pH to 4.0. Yellow powdery crystals of pyrido[2,3-c]-acridine-1-hydroxy-7-phenyl-2-carboxylic acid.hydrochloride precipitated. The crystals were collected by suction filtration, and dried to afford 0.85 g of the product. The elemental analysis values for $C_{33}H_{15}N_2O_3Cl$ were as follows:

|  | C(%) | H(%) | N(%) | Cl(%) |
|---|---|---|---|---|
| Calculated: | 68.58 | 3.75 | 6.95 | 8.80 |
| Found: | 68.20 | 3.61 | 7.08 | 8.91 |

EXAMPLE 4

1. 0.5 g of 9-butyl-3-amino-acridine [III] was mixed with 0.9 g of diethyl ethoxymethylenemalonate, and the mixture was heated at 95° to 100° C. for 90 minutes. The resulting reaction mixture was allowed to cool and thus solidified. The solidified product was recrystallized from a mixture of 1 ml of benzene and 8 ml of n-hexane to afford 0.7 g of 3-(β-diethoxycarbonylvinylamino)-9-butyl-acridine [III] as yellow needle-like crystals having a melting point of 108° to 110° C.

2. 0.5 g of the 3-(β-diethoxycarbonylvinylamino)-9-butylacridine obtained in (1) above was mixed with 5 ml of diphenyl ether, and the mixture was heated under reflux at 260° to 270° C. for 20 minutes. After cooling, 20 ml of n-hexane was added, and the precipitated crystals were collected by filtration. There was obtained 0.4 g of ethyl pyrido[2,3-c]-acridine-1-hydroxy-7-butyl-2-carboxylate [I] as yellow crystals having a melting point of 158° to 161° C.

3. 0.3 g of the ethyl ester [I] obtained in (3) above was added to a mixture of 6 ml of 6N-hydrochloric acid and 6 ml of acetic acid, and the mixture was heated at 95° to 100° C. for 30 minutes. After concentrating the solvent, the reaction mixture was cooled. The precipitated yellow needle-like crystals were collected by filtration and washed with ethanol to afford 0.24 g of pyrido[2,3-c]-acridine-1-hydroxy-7-butyl-2-carboxylic acid.hydrochloride having a decomposition point of about 300° C.

EXAMPLE 5

1. The procedure of Example 4, (1) was repeated except that 0.5 g of 9-ethyl-3-amino-acridine [III] and 1.0 g of diethyl ethoxymethylenemalonate [VI] were used instead of the 9-butyl-3-aminoacridine and the diethyl ethoxymethylenemalonate. There was obtained 0.7 g of 3-(β-diethoxycarbonylvinylamino)-9-ethylacridine [II] as yellow pillar-like crystals having a melting point of 134° to 136° C.

2. The procedure of Example 4, (2) was repeated except that the 3-(β-diethoxycarbonylvinylamino)-9-ethyl-acridine obtained in (1) above was used instead of the 3-(β-diethoxycarbonylvinylamino)-9-butyl-acridine. There was obtained 0.42 g of ethyl pyrido[2,3-c]-acridine-1-hydroxy-7-ethyl-2-carboxylate as yellow needle-like crystals having melting point of 172° to 176° C.

3. The procedure of Example 4, (3) was repeated except that the ethyl ester obtained in (2) above was used instead of the ethyl ester used in Example 4, (3). There was obtained 0.26 g of pyrido[2,3-c]-acridine-1-hydroxy-7-ethyl-2-carboxylic acid.hydrochloride as yellow scale-like crystals having a decomposition point of 310° to 320° C.

EXAMPLE 6

1. The procedure of Example 4, (1) was repeated except that 9-methyl-3-amino-acridine was used instead of the 9-butyl-3-amino-acridine. There was obtained 0.65 g of 3-(β-diethoxycarbonylvinylamino)-9-methylacridine [II] as a brown powder having a melting point of 148° to 151° C.

2. The procedure of Example 4, (2) was repeated except that the 3-(β-diethoxycarbonylvinylamino)-9-methyl-acridine obtained in (1) above was used instead of the 3-(β-diethoxycarbonylvinylamino)-9-butyl-acridine used in Example 4, (2). There was obtained 0.35 g of ethyl pyrido[2,3-c]-acridine-1-hydroxy-7-methyl-2-carboxylate [I] as a yellow powder having a melting point of 173° to 179° C.

3. The procedure of Example 4, (3) was repeated except that the ethyl ester obtained in (2) above was used instead of the ethyl ester used in Example 4, (3). There was obtained 0.25 g of pyrido [2,3-c]-acridine-1-hydroxy-7-methyl-2-carboxylic acid.hydrochloride as yellow crystals having a decomposition point of above 300° C.

EXAMPLE 7

1. The procedure of Example 4, (1) was repeated except that 7-methyl-3-amino-acridine was used instead of the 9-butyl-3-amino-acridine used in Example 4, (1). There was obtained 0.65 g of 3-(β-diethoxycarbonvinylamino)-7-methyl-acridine [II] as yellow needle-like crystals having a melting point of 150° to 152° C.

2. The procedure of Example 4, (2) was repeated except that the 3-(β-diethoxycarbonylvinylamino)-7-methylacridine obtained in (1) above was used instead of the 3-(β-diethoxycarbonylvinylamino)-9-butyl-acridine used in Example 4, (2). There was obtained 0.4 g of ethyl pyrido[2,3-c]-acridine-1-hydroxy-9-methyl-2-carboxylate [I] as yellow needle-like crystals having a melting point of 208° to 212° C.

3. The procedure of Example 4, (3) was repeated except that the ethyl ester obtained in (2) above was used instead of the ethyl ester used in Example 4, (3). There was obtained 0.24 g of pyrido[2,3-c]-acridine-1-hydroxy-9-methyl-2-carboxylic acid.hydrochloride as yellow needle-like crystals having a decomposition point of above 320° C.

EXAMPLE 8

In section (3) of each of Examples 1 to 7 above, the same procedure was repeated except that sulfuric acid or nitric acid was used instead of hydrochloric acid. The corresponding sulfates or nitrates was obtained. Each of these inorganic acid salts was dissolved in a dilute aqueous solution of sodium hydroxide, and the solution was added to an aqueous solution of lactic acid or tartaric acid. The mixture was stirred at room temperature for about 30 minutes. The resulting crystals were collected by filtration to afford lactates or tartrates of these compounds.

EXAMPLE 9

The procedure of Example 4 was repeated except that each of the substituted-3-amino-acridines corresponding to $R_1$ to $R_3$ of formula (I) shown in Table 2 below was used. The resulting acid salt was dissolved in a dilute aqueous solution of sodium hydroxide at room temperature with stirring for 30 minutes. Then, the solution was acidified with acetic acid, and the resulting crystals were collected by filtration to afford pyrido[2,3-c]-acridine-1-hydroxy-(5-, 7-, 9- and/or 11-substituted)-2-carboxylic acids shown in Table 2.

Table 2

| Compound No. | |
|---|---|
| F-638 | Pyrido Pyrido[2,3-c]-acridine-1-hydroxy-11-methyl-2-carboxylic acid |
| F-639 | Pyrido[2,3-c]-acridine-1-hydroxy-5-ethyl-2-carboxylic acid |
| F-640 | Pyrido[2,3-c]-acridine-1-hydroxy-9-ethyl-2-carboxylic acid |
| F-641 | Pyrido[2,3-c]-acridine-1-hydroxy-11-ethyl-2-carboxylic acid |
| F-642 | Pyrido[2,3-c]-acridine-1-hydroxy-5-n-propyl-2-carboxylic acid |
| F-643 | Pyrido[2,3-c]-acridine-1-hydroxy-7-n-propyl-2-carboxylic acid |
| F-644 | Pyrido[2,3-c]-acridine-1-hydroxy-9-n-propyl-2-carboxylic acid |
| F-645 | Pyrido[2,3-c]-acridine-1-hydroxy-10-n-propyl-2-carboxylic acid |
| F-646 | Pyrido[2,3-c]-acridine-1-hydroxy-5-isopropyl-2-carboxylic acid |
| F-647 | Pyrido[2,3-c]-acridine-1-hydroxy-7-isopropyl-2-carboxylic acid |
| F-648 | Pyrido[2,3-c]-acridine-1-hydroxy-9-isopropyl-2-carboxylic acid |
| F-649 | Pyrido[2,3-c]-acridine-1-hydroxy-10-isopropyl-2-carboxylic acid |
| F-650 | Pyrido[2,3-c]-acridine-1-hydroxy-5-n-butyl-2-carboxylic acid |
| F-651 | Pyrido[2,3-c]-acridine-1-hydroxy-9-n-butyl-2-carboxylic acid |
| F-652 | Pyrido[2,3-c]-acridine-1-hydroxy-10-n-butyl-2-carboxylic acid |
| F-653 | Pyrido[2,3-c]-acridine-1-hydroxy-5-sec-butyl-2-carboxylic acid |
| F-654 | Pyrido[2,3-c]-acridine-1-hydroxy-7-sec-butyl-2-carboxylic acid |
| F-655 | Pyrido[2,3-c]-acridine-1-hydroxy-9-sec-butyl-2-carboxylic acid |
| F-656 | Pyrido[2,3-c]-acridine-1-hydroxy-10-sec-butyl-2-carboxylic acid |
| F-657 | Pyrido[2,3-c]-acridine-1-hydroxy-5-tert-butyl-2-carboxylic acid |
| F-658 | Pyrido[2,3-c]-acridine-1-hydroxy-7-tert.-butyl-2-carboxylic acid |
| F-659 | Pyrido[2,3-c]-acridine-1-hydroxy-9-tert.-butyl-2-carboxylic acid |
| F-660 | Pyrido[2,3-c]-acridine-1-hydroxy-10-tert.-butyl-2-carboxylic acid |
| F-661 | Pyrido[2,3-c]-acridine-1-hydroxy-5-n-pentyl-2-carboxylic acid |
| F-662 | Pyrido[2,3-c]-acridine-1-hydroxy-7-n-pentyl-2-carboxylic acid |
| F-663 | Pyrido[2,3-]-acridine-1-hydroxy-9-n-pentyl-2-carboxylic acid |
| F-664 | Pyrido[2,3-c]-acridine-1-hydroxy-10-n-pentyl-2-carboxylic acid |
| F-665 | Pyrido[2,3-c]-acridine-1-hydroxy-5-iso-pentyl-2-carboxylic acid |
| F-666 | Pyrido[2,3-c]-acridine-1-hydroxy-7-iso-pentyl-2-carboxylic acid |
| F-667 | Pyrido[2,3-c]-acridine-1-hydroxy-9-iso-pentyl-2-carboxylic acid |
| F-668 | Pyrido[2,3-c]-acridine-1-hydroxy-10-iso-pentyl-2-carboxylic acid |
| F-669 | Pyrido[2,3-c]-acridine-1-hydroxy-5-tert.-pentyl-2-carboxylic acid |
| F-670 | Pyrido[2,3-c]-acridine-1-hydroxy-7-tert.-pentyl-2-carboxylic acid |
| F-671 | Pyrido[2,3-c]-acridine-1-hydroxy-9-tert.-pentyl-2-carboxylic acid |
| F-672 | Pyrido[2,3-c]-acridine-1-hydroxy-10-tert.-pentyl-2-carboxylic acid |
| F-673 | Pyrido[2,3-c]-acridine-1-hydroxy-5-(2'-methyl-n-butyl)-2-carboxylic acid |
| F-674 | Pyrido[2,3-c]-acridine-1-hydroxy-7-(2'-methyl-n-butyl)-2-carboxylic acid |
| F-675 | Pyrido[2,3-c]-acridine-1-hydroxy-9-(2'-methyl-n-butyl)-2-carboxylic acid |
| F-676 | Pyrido[2,3-c]-acridine-1-hydroxy-10-(2'-methyl-n-butyl)-2-carboxylic acid |
| F-677 | Pyrido(2,3-c]-acridine-1-hydroxy-5-n-hexyl-2-carboxylic acid |
| F-678 | Pyrido[2,3-c]-acridine-1-hydroxy-7-n-hexyl-2-carboxylic acid |
| F-679 | Pyrido[2,3-c]-acridine-1-hydroxy-9-n-hexyl-2-carboxylic acid |
| F-680 | Pyrido[2,3-c]-acridine-1-hydroxy-10-n-hexyl-2-carboxylic acid |
| F-681 | Pyrido[2,3-c]-acridine-1-hydroxy-5-n-heptyl-2-carboxylic acid |
| F-682 | Pyrido[2,3-c]-acridine-1-hydroxy-7-n-heptyl-2-carboxylic acid |
| F-683 | Pyrido[2,3-c]-acridine-1-hydroxy-9-n-heptyl-2-carboxylic acid |
| F-684 | Pyrido[2,3-c]-acridine-1-hydroxy-10-n-heptyl-2-carboxylic acid |
| F-685 | Pyrido[2,3-c]-acridine-1-hydroxy-5-n-decyl-2-carboxylic acid |
| F-686 | Pyrido[ 2,3-c]-acridine-1-hydroxy-7-n-decyl-2-carboxylic acid |
| F-687 | Pyrido[2,3-c]-acridine-1-hydroxy-9-n-decyl-2-carboxylic acid |
| F-688 | Pyrido[2,3-c]-acridine-1-hydroxy-10-n-decyl-2-carboxylic acid |
| F-689 | Pyrido[2,3-c]-acridine-1-hydroxy-5-vinyl-2-carboxylic acid |
| F-690 | Pyrido[2,3-c]-acridine-1-hydroxy-7-vinyl-2-carboxylic acid |
| F-691 | Pyrido[2,3-c]-acridine-1-hydroxy-9-vinyl-2-carboxylic acid |
| F-692 | Pyrido[2,3-c]-acridine-1-hydroxy-10-vinyl-2-carboxylic acid |
| F-693 | Pyrido[2,3-c]-acridine-1-hydroxy-5-allyl-2-carboxylic acid |
| F-694 | Pyrido[2,3-c]-acridine-1-hydroxy-7-allyl-2-carboxylic acid |
| F-695 | Pyrido[2,3-c]-acridine-1-hydroxy-9-allyl-2-carboxylic acid |
| F-696 | Pyrido[2,3-c]-acridine-1-hydroxy-10-allyl-2-carboxylic acid |
| F-697 | Pyrido[2,3-c]-acridine-1-hydroxy-5-propenyl-2-carboxylic acid |
| F-698 | Pyrido[2,3-c]-acridine-1-hydroxy-7-propenyl-2-carboxylic acid |
| F-699 | Pyrido[2,3-c]-acridine-1-hydroxy-9-propenyl-2-carboxylic acid |
| F-700 | Pyrido[2,3-c]-acridine-1-hydroxy-10-propenyl-2-carboxylic acid |
| F-701 | Pyrido[2,3-c]-acridine-1-hydroxy-5-(1'-butenyl)-2-carboxylic acid |
| F-702 | Pyrido[2,3-c]-acridine-1-hydroxy-7-(1'-butenyl)-2-carboxylic acid |
| F-703 | Pyrido[2,3-c]-acridine-1-hydroxy-9-(1'-butenyl)- |

Table 2-continued

| Compound No. | |
|---|---|
| F-704 | Pyrido[2,3-c]-acridine-1-hydroxy-10-(1'-butenyl)-2-carboxylic acid |
| F-705 | Pyrido[2,3-c]-acridine-1-hydroxy-5-(1'-pentenyl)-2-carboxylic acid |
| F-706 | Pyrido[2,3-c]-acridine-1-hydroxy-7-(1'-pentenyl)-2-carboxylic acid |
| F-707 | Pyrido[2,3-c]-acridine-1-hydroxy-9-(1'-pentenyl)-2-carboxylic acid |
| F-708 | Pyrido[2,3-c]-acridine-1-hydroxy-10-(1'-pentenyl)-2-carboxylic acid |
| F-709 | Pyrido[2,3-c]-acridine-1-hydroxy-5-(1'-hexenyl)-2-carboxylic acid |
| F-710 | Pyrido[2,3-c]-acridine-1-hydroxy-7-(1'-hexenyl)-2-carboxylic acid |
| F-711 | Pyrido[2,3-c]-acridine-1-hydroxy-9-(1'-hexenyl)-2-carboxylic acid |
| F-712 | Pyrido[2,3-c]-acridine-1-hydroxy-10-(1'-hexenyl)-2-carboxylic acid |
| F-713 | Pyrido[2,3-c]-acridine-1-hydroxy-5-phenyl-2-carboxylic acid |
| F-714 | Pyrido[2,3-c]-acridine-1-hydroxy-9-phenyl-2-carboxylic acid |
| F-715 | Pyrido[2,3-c]-acridine-1-hydroxy-10-phenyl-2-carboxylic acid |
| F-716 | Pyrido[2,3-c]-acridine-1-hydroxy-5-o-tolyl-2-carboxylic acid |
| F-717 | Pyrido[2,3-c]-acridine-1-hydroxy-7-o-tolyl-2-carboxylic acid |
| F-718 | Pyrido[2,3-c]-acridine-1-hydroxy-9-o-tolyl-2-carboxylic acid |
| F-719 | Pyrido[2,3-c]-acridine-1-hydroxy-10-o-tolyl-2-carboxylic acid |
| F-720 | Pyrido[2,3-c]-acridine-1-hydroxy-5-p-tolyl-2-carboxylic acid |
| F-721 | Pyrido[2,3-c]-acridine-1-hydroxy-7-p-tolyl-2-carboxylic acid |
| F-722 | Pyrido[2,3-c]-acridine-1-hydroxy-9-p-tolyl-2-carboxylic acid |
| F-723 | Pyrido[2,3-c]-acridine-1-hydroxy-10-p-tolyl-2-carboxylic acid |
| F-724 | Pyrido[2,3-c]-acridine-1-hydroxy-5-(2',3'-dimethylphenyl)-2-carboxylic acid |
| F-724 | Pyrido[2,3-c]-acridine-1-hydroxy-7-(2',3'-dimethylphenyl)-2-carboxylic acid |
| F-726 | Pyrido[2,3-c]-acridine-1-hydroxy-9-(2',3'-dimethylphenyl)-2-carboxylic acid |
| F-727 | Pyrido[2,3-c]-acridine-1-hydroxy-10-(2',3'-dimethylphenyl)-2-carboxylic acid |
| F-728 | Pyrido[2,3-c]-acridine-1-hydroxy-5-(2',4'-dimethylphenyl)-2-carboxylic acid |
| F-729 | Pyrido[2,3-c]-acridine-1-hydroxy-7-(2',4'-dimethylphenyl)-2-carboxylic acid |
| F-730 | Pyrido[2,3-c]-acridine-1-hydroxy-9-(2',4'-dimethylphenyl)-2-carboxylic acid |
| F-731 | Pyrido[2,3-c]-acridine-1-hydroxy-10-(2',4'-dimethylphenyl)-2-carboxylic acid |
| F-732 | Pyrido[2,3-c]-acridine-1-hydroxy-5-mesityl-2-carboxylic acid |
| F-733 | Pyrido[2,3-c]-acridine-1-hydroxy-7-mesityl-2-carboxylic acid |
| F-734 | Pyrido[2,3-c]-acridine-1-hydroxy-9-mesityl-2-carboxylic acid |
| F-735 | Pyrido[2,3-c]-acridine-1-hydroxy-10-mesityl-2-carboxylic acid |
| F-736 | Pyrido[2,3-c]-acridine-1-hydroxy-5-o-ethylphenyl-2-carboxylic acid |
| F-737 | Pyrido[2,3-c]-acridine-1-hydroxy-7-o-ethylphenyl-2-carboxylic acid |
| F-738 | Pyrido[2,3-c]-acridine-1-hydroxy-9-o-ethylphenyl-2-carboxylic acid |
| F-739 | Pyrido[2,3-c]-acridine-1-hydroxy-10-o-ethylphenyl-2-carboxylic acid |
| F-740 | Pyrido[2,3-c]-acridine-1-hydroxy-5-p-ethylphenyl-2-carboxylic acid |
| F-741 | Pyrido[2,3-c]-acridine-1-hydroxy-7-p-ethylphenyl-2-carboxylic acid |
| F-742 | Pyrido[2,3-c]-acridine-1-hydroxy-9-p-ethylphenyl-2-carboxylic acid |
| F-743 | Pyrido[2,3-c]-acridine-1-hydroxy-10-p-ethylphenyl-2-carboxylic acid |
| F-744 | Pyrido[2,3-c]-acridine-1-hydroxy-5-o-n-propylphenyl-2-carboxylic acid |
| F-745 | Pyrido[2,3-c]-acridine-1-hydroxy-7-o-n-propylphenyl-2-carboxylic acid |
| F-746 | Pyrido[2,3-c]-acridine-1-hydroxy-9-o-n-propylphenyl-2-carboxylic acid |
| F-747 | Pyrido[2,3-c]-acridine-1-hydroxy-10-o-n-propylphenyl-2-carboxylic acid |
| F-748 | Pyrido[2,3-c]-acridine-1-hydroxy-5-p-n-propylphenyl-2-carboxylic acid |
| F-749 | Pyrido[2,3-c]-acridine-1-hydroxy-7-p-n-propylphenyl-2-carboxylic acid |
| F-750 | Pyrido[2,3-c]-acridine-1-hydroxy-9-p-n-propylphenyl-2-carboxylic acid |
| F-751 | Pyrido[2,3-c]-acridine-1-hydroxy-10-p-n-propylphenyl-2-carboxylic acid |
| F-752 | Pyrido[2,3-c]-acridine-1-hydroxy-5-o-isopropylphenyl-2-carboxylic acid |
| F-753 | Pyrido[2,3-c]-acridine-1-hydroxy-7-o-isopropylphenyl-2-carboxylic acid |
| F-754 | Pyrido[2,3-c]-acridine-1-hydroxy-9-o-isopropylphenyl-2-carboxylic acid |
| F-755 | Pyrido[2,3-c]-acridine-1-hydroxy-10-o-isopropylphenyl-2-carboxylic acid |
| F-756 | Pyrido[2,3-c]-acridine-1-hydroxy-5-p-isopropylphenyl-2-carboxylic acid |
| F-757 | Pyrido[2,3-c]-acridine-1-hydroxy-7-p-isopropylphenyl-2-carboxylic acid |
| F-758 | Pyrido[2,3-c]-acridine-1-hydroxy-9-p-isopropylphenyl-2-carboxylic acid |
| F-759 | Pyrido[2,3-c]-acridine-1-hydroxy-10-p-isopropylphenyl-2-carboxylic acid |
| F-760 | Pyrido[2,3-c]-acridine-1-hydroxy-5-p-n-butylphenyl-2-carboxylic acid |
| F-761 | Pyrido[2,3-c]-acridine-1-hydroxy-7-p-n-butylphenyl-2-carboxylic acid |
| F-762 | Pyrido[2,3-c]-acridine-1-hydroxy-9-p-n-butylphenyl-2-carboxylic acid |
| F-763 | Pyrido[2,3-c]-acridine-1-hydroxy-10-p-n-butylphenyl-2-carboxylic acid |
| F-764 | Pyrido[2,3-c]-acridine-1-hydroxy-5-p-fluorophenyl-2-carboxylic acid |
| F-765 | Pyrido[2,3-c]-acridine-1-hydroxy-7-p-fluorophenyl-2-carboxylic acid |
| F-766 | Pyrido[2,3-c]-acridine-1-hydroxy-9-n-fluorophenyl-2-carboxylic acid |
| F-767 | Pyrido[2,3-c]-acridine-1-hydroxy-10-p-fluorophenyl-2-carboxylic acid |
| F-768 | Pyrido[2,3-c]-acridine-1-hydroxy-5-o-chlorophenyl-2-carboxylic acid |
| F-769 | Pyrido[2,3-c]-acridine-1-hydroxy-7-o-chlorophenyl-2-carboxylic acid |
| F-770 | Pyrido[2,3-c]-acridine-1-hydroxy-9-o-chlorophenyl-2-carboxylic acid |
| F-771 | Pyrido[2,3-c]acridine-1-hydroxy-10-o-chlorophenyl-2-carboxylic acid |
| F-772 | Pyrido[2,3-c]-acridine-1-hydroxy-5-p-chlorophenyl-2-carboxylic acid |
| F-773 | Pyrido[2,3-c]-acridine-1-hydroxy-7-p-chlorophenyl-2-carboxylic acid |
| F-774 | Pyrido[2,3-c]-acridine-1-hydroxy-9-p-chlorophenyl-2-carboxylic acid |
| F-775 | Pyrido[2,3-c]-acridine-1-hydroxy-10-p-chlorophenyl-2-carboxylic acid |
| F-776 | Pyrido[2,3-c]-acridine-1-hydroxy-5-o-bromophenyl-2-carboxylic acid |
| F-777 | Pyrido[2,3-c]-acridine-1-hydroxy-7-o-bromophenyl-2-carboxylic acid |
| F-778 | Pyrido[2,3-c]-acridine-1-hydroxy-9-o-bromophenyl-2-carboxylic acid |
| F-779 | Pyrido[2,3-c]-acridine-1-hydroxy-10-o-bromophenyl-2-carboxylic acid |
| F-780 | Pyrido[2,3-c]-acridine-1-hydroxy-5-o-bromophenyl-2-carboxylic acid |
| F-781 | Pyrido[2,3-c]-acridine-1-hydroxy-7-o-bromophenyl-2-carboxylic acid |
| F-782 | Pyrido[2,3-c]-acridine-1-hydroxy-9-p-bromophenyl-2-carboxylic acid |
| F-783 | Pyrido[2,3-c]-acridine-1-hydroxy-10-p-bromophenyl-2-carboxylic acid |
| F-784 | Pyrido[2,3-c]-acridine-1-hydroxy-5-o-iodophenyl-2-carboxylic acid |
| F-785 | Pyrido[2,3-c]-acridine-1-hydroxy-7-o-iodophenyl-2-carboxylic acid |
| F-786 | Pyrido[2,3-c]-acridine-1-hydroxy-9-o-iodophenyl-2-carboxylic acid |
| F-787 | Pyrido[2,3-c]-acridine-1-hydroxy-10-o-iodophenyl-2-carboxylic acid |
| F-788 | Pyrido[2,3-c]-acridine-1-hydroxy-5-p-iodophenyl-2-carboxylic acid |
| F-789 | Pyrido[2,3-c]-acridine-1-hydroxy-7-p-iodophenyl-2-carboxylic acid |
| F-790 | Pyrido[2,3-c]-acridine-1-hydroxy-9-p-iodophenyl-2-carboxylic acid |
| F-791 | Pyrido[2,3-c]-acridine-1-hydroxy-10-p-iodophenyl-2-carboxylic acid |
| F-792 | Pyrido[2,3-c]-acridine-1-hydroxy-5-m-nitrophenyl-2-carboxylic acid |
| F-793 | Pyrido[2,3-c]-acridine-1-hydroxy-7-m-nitrophenyl-2-carboxylic acid |
| F-794 | Pyrido[2,3-c]-acridine-1-hydroxy-9-m-nitrophenyl-2-carboxylic acid |
| F-795 | Pyrido[2,3-c]-acridine-1-hydroxy-10-m- |

Table 2-continued

| Compound No. | |
|---|---|
| F-796 | Pyrido[2,3-c]-acridine-1-hydroxy-5-nitrophenyl-2-carboxylic acid |
| F-797 | Pyrido[2,3-c]-acridine-1-hydroxy-5-o-hydroxyphenyl-2-carboxylic acid |
| F-798 | Pyrido[2,3-c]-acridine-1-hydroxy-7-o-hydroxyphenyl-2-carboxylic acid |
| F-779 | Pyrido[2,3-c]-acridine-1-hydroxy-9-o-hydroxyphenyl-2-carboxylic acid |
| F-800 | Pyrido[2,3-c]-acridine-1-hydroxy-10-o-hydroxyphenyl-2-carboxylic acid |
| F-801 | Pyrido[2,3-c]-acridine-1-hydroxy-5-p-hydroxyphenyl-2-carboxylic acid |
| F-802 | Pyrido[2,3-c]-acridine-1-hydroxy-7-p-hydroxyphenyl-2-carboxylic acid |
| F-803 | Pyrido[2,3-c]-acridine-1-hydroxy-p-hydroxyphenyl-2-carboxylic acid |
| F-804 | Pyrido[2,3-c]-acridine-1-hydroxy-10-p-hydroxyphenyl-2-carboxylic acid |
| F-805 | Pyrido[2,3-c]-acridine-1-hydroxy-5-o-methoxyphenyl-2-carboxylic acid |
| F-806 | Pyrido[2,3-c]-acridine-1-hydroxy-7-o-methoxyphenyl-2-carboxylic acid |
| F-807 | Pyrido[2,3-c]-acridine-1-hydroxy-9-o-methoxyphenyl-2-carboxylic acid |
| F-808 | Pyrido[2,3-c]-acridine-1-hydroxy-10-o-methoxyphenyl-2-carboxylic acid |
| F-809 | Pyrido[2,3-c]-acridine-1-hydroxy-5-p-methoxyphenyl-2-carboxylic acid |
| F-810 | Pyrido[2,3-c]-acridine-1-hydroxy-7-p-methoxyphenyl-2-carboxylic acid |
| F-811 | Pyrido[2,3-c]-acridine-1-hydroxy-9-p-methoxyphenyl-2-carboxylic acid |
| F-812 | Pyrido[2,3-c]-acridine-1-hydroxy-10-p-methoxyphenyl-2-carboxylic acid |
| F-813 | Pyrido[2,3-c]-acridine-1-hydroxy-5-o-ethoxyphenyl-2-carboxylic acid |
| F-814 | Pyrido[2,3-c]-acridine-1-hydroxy-7-o-ethoxyphenyl-2-carboxylic acid |
| F-815 | Pyrido[2,3-c]-acridine-1-hydroxy-9-o-ethoxyphenyl-2-carboxylic acid |
| F-816 | Pyrido[2,3-c]-acridine-1-hydroxy-10-O-ethoxyphenyl-2-carboxylic acid |
| F-817 | Pyrido[2,3-c]-acridine-1-hydroxy-5-(1-naphthyl)-2-carboxylic acid |
| F-818 | Pyrido[2,3-c]-acridine-1-hydroxy-7-(1-naphthyl)-2-carboxylic acid |
| F-819 | Pyrido[2,3-c]-acridine-1-hydroxy-9-(1-naphthyl)-2-carboxylic acid |
| F-820 | Pyrido[2,3-c]-acridine-1-hydroxy-10-(1-naphthyl)-2-carboxylic acid |
| F-821 | Pyrido[2,3-c]-acridine-1-hydroxy-5-methoxy-2-carboxylic acid |
| F-822 | Pyrido[2,3-c]-acridine-1-hydroxy-7-methoxy-2-carboxylic acid |
| F-823 | Pyrido[2,3-c]-acridine-1-hydroxy-9-methoxy-2-carboxylic acid |
| F-824 | Pyrido[2,3-c]-acridine-1-hydroxy-11-methoxy-2-carboxylic acid |
| F-825 | Pyrido[2,3-c]-acridine-1-hydroxy-5-ethoxy-2-carboxylic acid |
| F-826 | yrido[2,3-c]-acridine-1-hydroxy-7-ethoxy-2-carboxylic acid |
| F-827 | Pyrido[2,3-c]-acridine-1-hydroxy-9-ethoxy-2-carboxylic acid |
| F-828 | Pyrido[2,3-c]-acridine-1-hydroxy-10-ethoxy-2-carboxylic acid |
| F-829 | Pyrido[2,3-c]-acridine-1-hydroxy-5-n-butoxy-2-carboxylic acid |
| F-830 | Pyrido[2,3-c]-acridine-1-hydroxy-7-n-butoxy-2-carboxylic acid |
| F-831 | Pyrido[2,3-c]-acridine-1-hydroxy-9-n-butoxy-2-carboxylic acid |
| F-832 | Pyrido[2,3-c]-acridine-1-hydroxy-10-n-butoxy-1-carboxylic acid |
| F-833 | Pyrido[2,3-c]-acridine-1-hydroxy-5-iso-butoxy-2-carboxylic acid |
| F-834 | Pyrido[2,3-c]-acridine-1-hydroxy-7-iso-butoxy-2-carboxylic acid |
| F-835 | Pyrido[2,3-c]-acridine-1-hydroxy-9-ixo-butoxy-2-carboxylic acid |
| F-836 | Pyrido[2,3-c]-acridine-1-hydroxy-10-is-butoxy-2-carboxylic acid |
| F-837 | Pyrido[2,3-c]-acridine-1-hydroxy-5-chloro-2-carboxylic acid |
| F-838 | Pyrido[2,3-c]-acridine-1-hydroxy-7-chloro-2-carboxylic acid |
| F-839 | Pyrido[2,3-c]-acridine-1-hydroxy-9-chloro-2-carboxylic acid |
| F-840 | Pyrido[2,3-c]-acridine-1-hydroxy-10-chloro-2-carboxylic acid |
| F-841 | Pyrido[2,3-c]-acridine-1-hydroxy-5-bromo-2-carboxylic acid |
| F-842 | Pyrido[2,3-c]-acridine-1-hydroxy-7-bromo-2-carboxylic acid |
| F-843 | Pyrido[2,3-c]-acridine-1-hydroxy-9-bromo-2-carboxylic acid |
| f-843 | Pyrido[2,3-c]-acridine-1-hydroxy-10-bromo-2-carboxylic acid |
| F-844 | Pyrido[2,3-c]-acridine-1-hydroxy-5-iodo-2-carboxylic acid |
| f-845 | Pyrido[2,3-c]-acridine-1-hydroxy-7-iodo-2-carboxylic acid |
| F-846 | yrido[2,3-c]-acridine-1-hydroxy-9-iodo-2-carboxylic acid |
| F-847 | Pyrido[2,3-c]-acridine-1-hydroxy-10-iodo-2-carboxylic acid |
| F-848 | Pyrido[2,3-c]-acridine-1-hydroxy-5-amino-2-carboxylic acid |
| F-849 | Pyrido[2,3-c]-acridine-1-hydroxy-7-amino-2-carboxylic acid |
| F-850 | Pyrido[2,3-c]-acridine-1-hydroxy-9-amino-2-carboxylic acid |
| F-851 | Pyrido[2,3-c]-acridine-1-hydroxy-11-amino-2-carboxylic acid |
| F-852 | Pyrido[2,3-c]-acridine-1-hydroxy-5-methylamino-2-carboxylic acid |
| F-853 | Pyrido[2,3-c]-acridine-1-hydroxy-7-methylamino-2-carboxylic acid |
| F-854 | Pyrido[2,3-c]-acridine-1-hydroxy-9-methylamino-2-carboxylic acid |
| F-855 | Pyrido[2,3-c]-acridine-1-hydroxy-11-methylamino-2-carboxylic acid |
| F-856 | Pyrido[2,3-c]-acridine-1-hydroxy-5-ethylamino-2-carboxylic acid |
| F-857 | Pyrido[2,3-c]-acridine-1-hydroxy-7-ethylamino-2-carboxylic acid |
| F-858 | Pyrido[2,3-c]-acridine-1-hydroxy-9-ethylamino-2-carboxylic acid |
| F-859 | Pyrido[2,3-c]-acridine-1-hydroxy-10-ethylamino-2-carboxylic acid |
| F-860 | Pyrido[2,3-c]-acridine-1-hydroxy-5-n-propylamino-2-carboxylic acid |
| F-861 | Pyrido[2,3-c]-acridine-1-hydroxy-7-n-propylamino-2-carboxylic acid |
| F-862 | Pyrido[2,3-c]-acridine-1-hydroxy-9-n-propylamino-2-carboxylic acid |
| F-863 | Pyrido[2,3-c]-acridine-1-hydroxy-10-n-propylamino-2-carboxylic acid |
| F-864 | Pyrido[2,3-c]-acridine-1-hydroxy-5-n-butylamino-2-carboxylic acid |
| F-865 | Pyrido[2,3-c]-acridine-1-hydroxy-7-n-butylamino-2-carboxylic acid |
| F-866 | Pyrido[2,3-c]-acridine-1-hydroxy-9-n-butylamino-2-carboxylic acid |
| F-867 | Pyrido[2,3-c]-acridine-1-hydroxy-10-n-butylamino-2-carboxylic acid |
| F-868 | Pyrido[2,3-c]-acridine-1-hydroxy-5-dimethylamino-2-carboxylic acid |
| F-869 | Pyrido[2,3-c]-acridine-1-hydroxy-7-dimethylamino-2-carboxylic acid |
| F-870 | Pyrido[2,3-c]-acridine-1-hydroxy-9-dimethylamino-2-carboxylic acid |
| F-871 | Pyrido[2,3-c]-acridine-1-hydroxy-10-dimethylamino-2-carboxylic acid |
| F-872 | Pyrido[2,3-c]-acridine-1-hydroxy-5-diethylamino-2-carboxylic acid |
| F-873 | Pyrido[2,3-c]-acridine-1-hydroxy-7-diethylamino-2-carboxylic acid |
| F-874 | Pyrido[2,3-c]-acridine-1-hydroxy-9-diethylamino-2-carboxylic acid |
| F-875 | Pyrido[2,3-c]-acridine-1-hydroxy-10-diethylamino-2-carboxylic acid |
| F-876 | Pyrido[2,3-c]-acridine-1-hydroxy-5-methylmercapto-2-carboxylic acid |
| F-877 | Pyrido[2,3-c]-acridine-1-hydroxy-7-methylmercapto-2-carboxylic acid |
| F-878 | Pyrido[2,3-c]-acridine-1-hydroxy-9-methylmercapto-2-carboxylic acid |
| F-879 | Pyrido[2,3-c]-acridine-1-hydroxy-10-methylmercapto-2-carboxylic acid |
| F-880 | Pyrido[2,3-c]-acridine-1-hydroxy-5-ethylmercapto-2-carboxylic acid |
| F-881 | Pyrido[2,3-c]-acridine-1-hydroxy-7-ethylmercapto-2-carboxylic acid |
| F-882 | Pyrido[2,3-c]-acridine-1-hydroxy-9-ethylmercapto-2-carboxylic acid |
| F-883 | Pyrido[2,3-c]-acridine-1-hydroxy-10-ethylmercapto-2-carboxylic acid |
| F-884 | Pyrido[2,3-c]-acridine-1-hydroxy-5-n-propylmercapto-2-carboxylic acid |
| F-885 | Pyrido[2,3-c]-acridine-1-hydroxy-7-n-propylmercapto-2-carboxylic acid |
| F-886 | Pyrido[2,3-c]-acridine-1-hydroxy-9-n-propylmercapto-2-carboxylic acid |
| F-887 | Pyrido[2,3-c]-acridine-1-hydroxy-10-n- |

Table 2-continued

| Compound No. | |
|---|---|
| F-888 | propylmercapto-2-carboxylic acid Pyrido[2,3-c]-acridine-1-hydroxy-5-methylsulfonyl-2-carboxylic acid |
| F-889 | Pyrido[2,3-c]-acridine-1-hydroxy-7-methylsulfonyl-2-carboxylic acid |
| F-890 | Pyrido[2,3-c]-acridine-1-hydroxy-9-methylsulfonyl-2-carboxylic acid |
| F-891 | Pyrido[2,3-c]-acridine-1-hydroxy-10-methylsulfonyl-2-carboxylic acid |
| F-892 | Pyrido[2,3-c]-acridine-1-hydroxy-10-nitro-2-carboxylic acid |
| F-893 | Pyrido[2,3-c]-acridine-1-hydroxy-5-hydroxymethyl-2-carboxylic acid |
| F-894 | Pyrido[2,3-c]-acridine-1-hydroxy-7-hydroxymethyl-2-carboxylic acid |
| F-895 | Pyrido[2,3-c]-acridine-1-hydroxy-9-hydroxymethyl-2-carboxylic acid |
| F-896 | Pyrido[2,3-c]-acridine-1-hydroxy-10-hydroxymethyl-2-carboxylic acid |
| F-897 | Pyrido[2,3-c]-acridine-1-hydroxy-5-(1'-hydroxyethyl)-2-carboxylic acid |
| F-898 | Pyrido[2,3-c]-acridine-1-hydroxy-7-(1'-hydroxyethyl)-2-carboxylic acid |
| F-899 | Pyrido[2,3-c]-acridine-1-hydroxy-9-(1'-hydroxyethyl)-2-carboxylic acid |
| F-900 | Pyrido[2,3-c]-acridine-1-hydroxy-10-(1'-hydroxyethyl)-2-carboxylic acid |
| F-901 | Pyrido[2,3-c]-acridine-1-hydroxy-5-aminomethyl-2-carboxylic acid |
| F-902 | Pyrido[2,3-c]-acridine-1-hydroxy-7-aminomethyl-2-carboxylic acid |
| F-903 | Pyrido[2,3-c]-acridine-1-hydroxy-9-aminomethyl-2-carboxylic acid |
| F-904 | Pyrido[2,3-c]-acridine-1-hydroxy-10-aminomethyl-2-carboxylic acid |
| F-905 | Pyrido[2,3-c]-acridine-1-hydroxy-5-(1'-aminoethyl)-2-carboxylic acid |
| F-906 | Pyrido[2,3-c]-acridine-1-hydroxy-7-(1'-aminoethyl)-2-carboxylic acid |
| F-907 | Pyrido[2,3-c]-acridine-1-hydroxy-9-(1'-aminoethyl)-2-carboxylic acid |
| F-908 | Pyrido[2,3-c]-acridine-1-hydroxy-10-(1'-aminoethyl)-2-carboxylic acid |
| F-909 | Pyrido[2,3-c]-acridine-1-hydroxy-5-(2'-amino-n-propyl)-2-carboxylic acid |
| F-910 | Pyrido[2,3-c]-acridine-1-hydroxy-7-(2'-amino-n-propyl)-2-carboxylic acid |
| F-911 | Pyrido[2,3-c]-acridine-1-hydroxy-9-(2'-amino-n-propyl)-2-carboxylic acid |
| F-912 | Pyrido[2,3-c]-acridine-1-hydroxy-10-(2'-amino-n-propyl)-2-carboxylic acid |
| F-913 | Pyrido[2,3-c]-acridine-1-hydroxy-5-di-(hydroxymethyl)amino-2-carboxylic acid |
| F-914 | Pyrido[2,3-c]-acridine-1-hydroxy-7-di-(hydroxymethyl)amino-2-carboxylic acid |
| F-915 | Pyrido[2,3-c]-acridine-1-hydroxy-9-di-(hydroxymethyl)amino-2-carboxylic acid |
| F-916 | Pyrido[2,3-c]-acridine-1-hydroxy-10-di-(hydroxymethyl)amino-2-carboxylic acid |
| F-917 | Pyrido[2,3-c]-acridine-1-hydroxy-5-di-(hydroxyethyl)amino-2-carboxylic acid |
| F-918 | Pyrido[2,3-c]-acridine-1-hydroxy-7-di-(hydroxyethyl)amino-2-carboxylic acid |
| F-919 | Pyrido[2,3-c]-acridine-1-hydroxy-9-di-(hydroxyethyl)amino-2-carboxylic acid |
| F-920 | Pyrido[2,3-c]-acridine-1-hydroxy-10-di-(hydroxyethyl)amino-2-carboxylic acid |
| F-921 | Pyrido[2,3-c]-acridine-1-hydroxy-5-acetoxymethylamino-2-carboxylic acid |
| F-922 | Pyrido[2,3-c]-acridine-1-hydroxy-7-acetoxymethylamino-2-carboxylic acid |
| F-923 | Pyrido[2,3-c]-acridine-1-hydroxy-9-acetoxymethylamino-2-carboxylic acid |
| F-924 | Pyrido[2,3-c]-acridine-1-hydroxy-10-acetoxymethylamino-2-carboxylic acid |
| F-925 | Pyrido[2,3-c]-acridine-1-hydroxy-5-acetoxyethylamino-2-carboxylic acid |
| F-926 | Pyrido[2,3-c]-acridine-1-hydrox-7-acetoxyethylamino-2-carboxylic acid |
| F-927 | Pyrido[2,3-c]-acridine-1-hydroxy-9-acetoxyethylamino-2-carboxylic acid |
| F-928 | Pyrido[2,3-c]-acridine-1-hydroxy-10-acetoxyethylamino-2-carboxylic acid |
| F-929 | Pyrido[2,3-c]-1,5-dihydroxy-2-carboxylic acid |
| F-930 | Pyrido[2,3-c]-1,7-dihydroxy-2-carboxylic acid |
| F-931 | Pyrido[2,3-c]-1,9-dihydroxy-2-carboxylic acid |
| F-932 | Pyrido[2,3-c]-1,11-dihydroxy-2-carboxylic acid |
| F-933 | Pyrido[2,3-c]-1-hydroxy-2,5-dicarboxylic acid |
| F-934 | Pyrido[2,3-c]-1-hydroxy-2,7-dicarboxylic acid |
| F-935 | Pyrido[2,3-c]-1-hydroxy-2,9-dicarboxylic acid |
| F-936 | Pyrido[2,3-c]-1-hydroxy-2,11-dicarboxylic acid |

EXAMPLES OF USE

Example 10

Some of the compounds of this invention were tested as to their antibacterial activity (MIC, mcg/ml) against Staph. aureus as Gram-positive bacterium and E. coli as Gram-negative bacterium. The results are shown in Table 3. In the table, the antibacterial activity of 0.09 to 1.25 mcg/ml. is indicated as $A_1$, and the antibacterial activity of more than 1.25 mcg/ml. and not more than 2.5 mcg/ml. is indicated as $A_2$.

Table 3

| | Antibacterial Activity | |
|---|---|---|
| Compound No. | Staph. aureus | E. coli |
| F-631 | $A_1$ | $A_1$ |
| F-632 | $A_1$ | $A_1$ |
| F-633 | $A_1$ | $A_1$ |
| F-634 | $A_1$ | $A_1$ |
| F-635 | $A_1$ | $A_1$ |
| F-636 | $A_1$ | $A_1$ |
| F-637 | $A_1$ | $A_1$ |
| F-929 | $A_1$ | $A_1$ |
| F-930 | $A_1$ | $A_1$ |
| F-931 | $A_1$ | $A_1$ |
| F-932 | $A_1$ | $A_1$ |
| F-777 | $A_1$ | $A_1$ |
| F-781 | $A_1$ | $A_1$ |
| F-789 | $A_1$ | $A_1$ |
| F-836 | $A_1$ | $A_1$ |
| F-840 | $A_1$ | $A_1$ |
| F-841 | $A_1$ | $A_1$ |
| F-844 | $A_1$ | $A_1$ |
| F-845 | $A_1$ | $A_1$ |
| F-690 | $A_2$ | $A_2$ |
| F-694 | $A_2$ | $A_1$ |
| F-820 | $A_2$ | $A_2$ |
| F-825 | $A_2$ | $A_1$ |
| F-849 | $A_2$ | $A_2$ |
| F-856 | $A_1$ | $A_1$ |
| F-858 | $A_1$ | $A_1$ |
| F-853 | $A_1$ | $A_1$ |
| F-869 | $A_1$ | $A_1$ |
| F-877 | $A_1$ | $A_1$ |
| F-889 | $A_1$ | $A_1$ |
| F-890 | $A_1$ | $A_1$ |
| F-892 | $A_1$ | $A_1$ |
| F-935 | $A_2$ | $A_2$ |
| F-893 | $A_2$ | $A_1$ |
| F-895 | $A_2$ | $A_1$ |
| F-913 | $A_1$ | $A_1$ |
| F-914 | $A_1$ | $A_1$ |
| F-915 | $A_1$ | $A_1$ |
| F-916 | $A_1$ | $A_1$ |
| F-901 | $A_2$ | $A_2$ |
| F-925 | $A_1$ | $A_1$ |
| F-926 | $A_1$ | $A_1$ |
| F-927 | $A_1$ | $A_1$ |

What we claim is:

1. A member selected from the group consisting of a compound of the formula

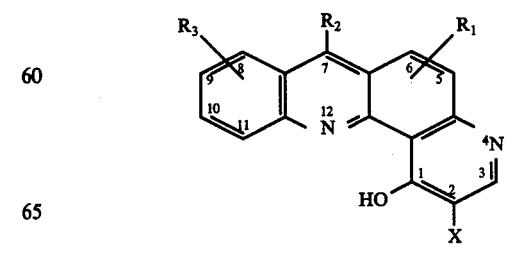

wherein X is a member selected from carboxy and $C_1$-$C_6$ alkoxy-containing carbalkoxy, and each of $R_1$, $R_2$ and $R_3$ is a member selected from the group consisting of (1) hydrogen, (2) $C_1$-$C_{10}$ alkyl, (3) $C_2$-$C_6$ alkyl-containing alkenyl, (4) $C_6$-$C_{10}$ aryl which is unsubstituted or substituted by a member of a group consisting of $C_1$-$C_5$ alkyl, halogen, nitro, $C_1$-$C_5$ alkylamino, hydroxy and $C_1$-$C_5$ alkoxy, (5) $C_1$-$C_4$ alkyl-containing alkylamino, (6) $C_1$-$C_6$ alkyl-containing alkylmercapto, (7) nitro, (8) cyano, (9) $C_1$-$C_2$ alkyl-containing alkylsulfonyl, (10) carboxy, (11) $C_1$-$C_6$ alkoxy-containing carbalkoxy, (12) $C_1$-$C_6$ alkyl-containing hydroxyalkyl, (13) $C_1$-$C_3$ alkyl-containing aminoalkyl, (14) $C_1$-$C_2$ hydroxyalkylamino, and (15) $C_1$-$C_2$ alkyl-containing acetoxyalkylamino and a pharmaceutically acceptable acid addition salt thereof.

2. A compound according to claim 1 wherein X is a member selected from the group consisting of carboxy and $C_1$-$C_6$ alkoxy-containing carbalkoxy, and each of $R_1$, $R_2$ and $R_3$ is a member selected from the group consisting (1) hydrogen, (2) $C_1$-$C_6$ alkyl, (3) $C_2$-$C_3$ alkenyl, (4) $C_6$-$C_{10}$ aryl which is unsubstituted or substituted by $C_1$-$C_5$ alkyl or $C_1$-$C_5$ alkylamino, (5) $C_1$-$C_4$ alkylamino, (6) nitro, (7) carboxy, (8) $C_1$-$C_6$ alkoxy-containing carbalkoxy and (9) $C_1$-$C_2$ hydroxyalkylamino.

3. An acid addition salt of a compound according to claim 2 wherein the acid is selected from the group consisting of hydrochloric acid, sulfuric acid, phosphoric acid, hydrobromic acid, nitric acid, acetic acid, propionic acid, lactic acid, butyric acid, malonic acid, tartaric acid, succinic acid and phthalic acid.

* * * * *